United States Patent [19]

Branemark

[11] Patent Number: 5,062,851

[45] Date of Patent: Nov. 5, 1991

[54] ANCHORING ELEMENT FOR SUPPORTING A JOINT MECHANISM OF A FINGER OR OTHER RECONSTRUCTED JOINT

[75] Inventor: Per-Ingvar Branemark, Mölndal, Sweden

[73] Assignee: Medevelop AB, Sweden

[21] Appl. No.: 406,586

[22] Filed: Sep. 13, 1989

[30] Foreign Application Priority Data

Apr. 25, 1989 [SE] Sweden ................... 8901508

[51] Int. Cl.⁵ .............................................. A61F 2/30
[52] U.S. Cl. ........................................ 623/18; 623/21; 623/16
[58] Field of Search ..................... 623/16, 18-22

[56] References Cited

U.S. PATENT DOCUMENTS

| | | | |
|---|---|---|---|
| 4,013,071 | 3/1977 | Rosenberg | 623/16 |
| 4,330,891 | 5/1982 | Branemark | 623/11 |
| 4,484,570 | 11/1984 | Sutte et al. | 606/72 |
| 4,911,719 | 3/1990 | Merle | 623/18 |
| 4,938,770 | 7/1990 | Frey et al. | 623/23 |
| 4,944,759 | 7/1990 | Mallary et al. | 623/22 |
| 4,955,916 | 9/1990 | Carignan et al. | 623/21 |
| 4,990,161 | 2/1991 | Kampner | 623/16 |
| 4,997,433 | 3/1991 | Goble et al. | 606/64 |

FOREIGN PATENT DOCUMENTS

| | | | |
|---|---|---|---|
| 0280424 | 8/1988 | European Pat. Off. | 623/21 |
| 88/03781 | 6/1988 | World Int. Prop. O. | 623/17 |
| 89/03663 | 5/1989 | World Int. Prop. O. | 623/18 |

*Primary Examiner*—David J. Isabella
*Assistant Examiner*—David H. Willse
*Attorney, Agent, or Firm*—Ostrolenk, Faber, Gerb & Soffen

[57] ABSTRACT

An anchoring element for supporting a joint mechanism is disclosed. The anchoring element is substantially rotationally symmetrical, at least partially hollow, and includes a material which is compatible with the tissue of a bone. The anchoring element has a surface which can be at least partially osseo-integrated with the tissue to achieve permanent endosteal anchorage in the longitudinal axis of the bone. The anchoring element is applied within the bone by: cutting the bone close to its joint to expose the marrow cavity of the bone; forming a space in the marrow cavity close to the joint; applying a guide sleeve in the space; and screwing the anchoring element into the marrow cavity while using the guide sleeve to center the anchoring element.

12 Claims, 5 Drawing Sheets

ANCHORING ELEMENT FOR SUPPORTING A JOINT MECHANISM OF A FINGER OR OTHER RECONSTRUCTED JOINT

BACKGROUND OF THE INVENTION

1. Field of the Invention

The present invention relates to an anchoring element for supporting a joint mechanism, a method of applying an anchoring element within a bone, and a reconstructed joint.

A preferred embodiment of the invention will be described in detail in the following with reference to the reconstruction of a finger joint. However, the invention is not limited thereto. The invention can be used for other similar joints, such as toe joints, elbow joints, and so on. The invention can also be used in reconstructions after amputation or other defects.

2. Description of the Related Art

Finger-joint reconstructions, entailing prostheses, are primarily carried out on MCP joints which have become rheumatically changed. Prostheses known for this purpose include Swanson Silastic finger joints. Such joints consist of a material similar to silicon, are elongate in shape, and have ends with substantially circular cross sections. The ends can be substantially circular cross sections. The ends can be fitted and anchored into the marrow cavity of each bone. The central portion of the prosthesis is elastically deformable and thus constitutes the actual joint mechanism.

The St. George prosthesis, a cemented prosthesis, is also known for finger-joint reconstructions.

A problem with these conventional prostheses is that the anchoring element supporting the actual prosthesis mechanism loosens (mainly due to bone resorption) with undesired displacement of the prosthesis in the direction of load.

Attempts have therefore been made in recent years to use titanium fixtures anchored in the marrow cavity of the bone with the object of becoming osseo-integrated as described by Hagert et al. "Metacarpophalangal Joint Replacement with Osseo-integrated Endoprostheses" in Scand. J. Plast. econstr Surg. 20, pages 207–218, 1986. It is already known to permanently anchor oral and extraoral prostheses in bone tissue. This dental osseo-integration technique has been developed over the last 25 years by Professor Branemark and his colleagues, with excellent results in applying fixtures in the jawbone to hold teeth or arch attachments. However, the experiments performed by Hagert to apply this technique to the reconstruction of finger joints has not fulfilled expectations. The unacceptable results are evidently due to the entirely different conditions encountered when using this "dental technique" in the prosthetic reconstruction of finger-joints. For example, in the known techniques, the fixture is anchored at right angles to the longitudinal axis of the bone. In the finger joint, the fixture is placed along the axis of the bone. Of course, this creates totally different loads and stresses on the anchoring elements.

Today, the main problem in orthopedic prosthesis surgery is still loosening of the bone anchoring unit. However, with a success rate for dental implants of more than 90% over a 20 year period, a number of other problems arise which, so far, have been unnecessary to take into account. One of the major problems is increased wear on the joint mechanism. A different type of prosthesis design from that used hitherto is required if the osseo-integration method is to be applied. To enable the joint mechanism to be replaced without disturbing the bone anchorage, the prosthesis system must be divided into components where the joint-mechanism element can be separated from the actual bone-anchoring element. Further, if the two-stage method is to be used, it must be possible to connect the joint mechanism in the second stage if the patient, or at least the patient's reconstructed joint, is not to be kept immobilized. Two factors must therefore be taken into account: First, the joint mechanism is subject to wear and therefore must be replaceable. Second, to use the two-stage method, the joint mechanism must be replaceable.

SUMMARY OF THE INVENTION

It has now surprisingly been found that the problems and drawbacks of the techniques described above can be eliminated by the present invention.

The invention is based on extensive experimental biological analysis of the structure and function of joints in the course of a disease or in defective state after wear or inflammatory decomposition of bone tissue and extensive studies of the vascular supply to the bone marrow. It has been established that, in the synthetic replacement of destroyed articular cartilage and ligament, bone and marrow tissue must be treated as a structural and functional unit. It is absolutely necessary to account for the cooperation between the bone and marrow tissue, particularly over a long period of time, if the hard tissue is to function as a support element.

The invention is thus based on the realization that, when anchoring a prosthetic replacement for a joint surface and ligament to parts of the skeleton close to a joint, the interaction between bone marrow and bone tissue must be respected. This means that an attachment element in the marrow cavity of a long bone must be anchored by mechanical elements which will permit communication between marrow and bone tissue along, as far as technically possible, the entire length of the anchoring element, paying particular attention to the boundary layer between marrow and compact bone in the wall of the marrow cavity.

Thus, the invention is directed to an anchoring element for supporting a joint mechanism, wherein the anchoring element is substantially rotationally symmetrical, at least partially hollow, and includes a material which is compatible with the tissue of a bone. The anchoring element has a surface which can be at least partially osseo-integrated with the tissue to achieve permanent endosteal anchorage in the longitudinal axis of the bone. The invention is also directed to a reconstructed joint.

The invention is also directed to a method of applying an anchoring element within a bone, comprising: cutting the bone close to its joint to expose the marrow cavity of the bone; forming a space in the marrow cavity close to the joint; applying a guide sleeve in the space; and screwing the anchoring element into the marrow cavity while using the guide sleeve to center the anchoring element.

Other features and advantages of the invention will become apparent from the following description of a preferred embodiment of the invention, with reference to the accompanying drawings.

DETAILED DESCRIPTION OF THE PREFERRED EMBODIMENT

Figure 1:
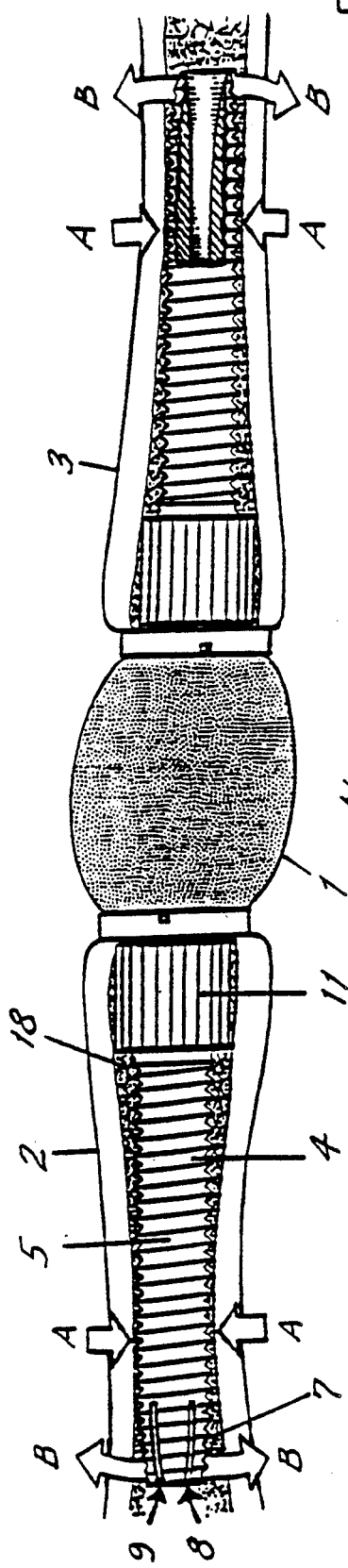
FIG. 1 is a partial cross-sectional view of a reconstructed finger joint with an anchoring element in accordance with the invention.

In FIG. 1, the parts of a long bone on each side of a finger joint mechanism 1 are designated 2 and 3, respectively.

A rotationally symmetrical anchoring element 4 is formed of a hollow, substantially sleeve-like body 5 with external threading 6 and decreasing wall thickness. The open insertion end 7 of the body 5 tapers and is provided with slits 8 and 9 initiating from the open end 7.

Figure 6:
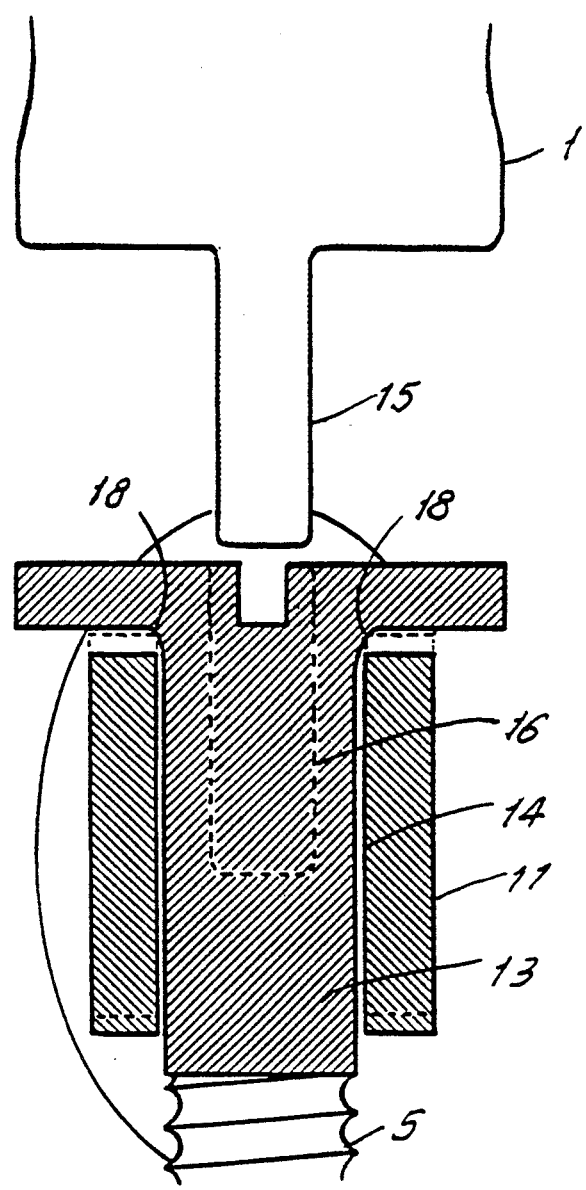
FIG. 6 is a partial cross-sectional view along the line 6—6 of FIG. 4, and illustrates a portion of the joint mechanism in accordance with the invention.
Figure 7:
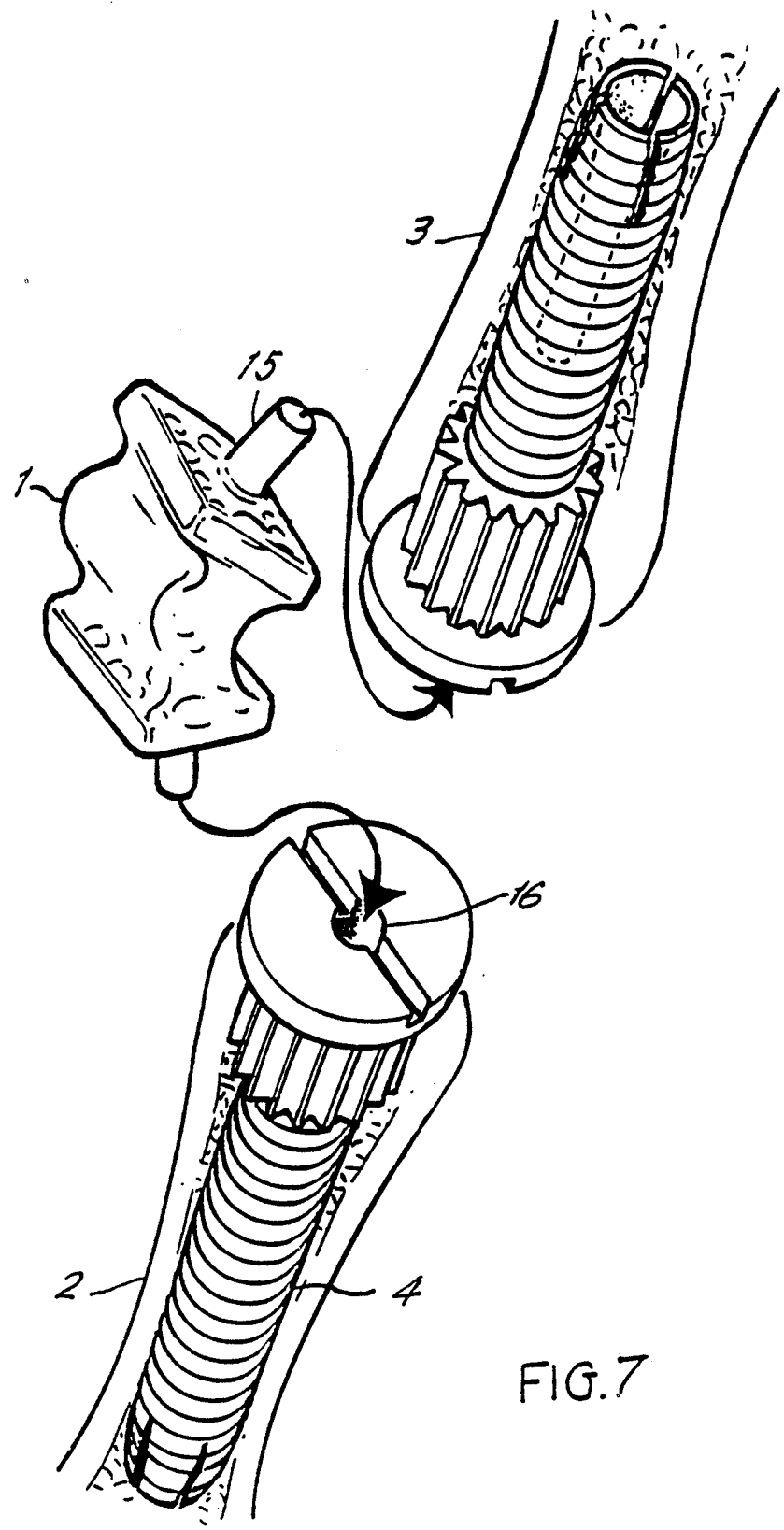
FIG. 7 illustrates the assembly of the joint mechanism to anchoring elements in accordance with the invention.

The end 13 (FIG. 6) of the anchoring element 4 closest to the joint mechanism 1 is located in a guide sleeve 11. The guide sleeve 11 surrounds the joint end 13. The joint end 13 of the body 5 is thus locked by a wedge effect against the inner surface 14 of the guide sleeve 11 when the body 5 has been screwed sufficiently far into the bone tissue. The joint end 13 detachably receives connection parts 15 of the joint mechanism 1. The connection parts 15 may be centered dowels (FIG. 7) protruding from the joint mechanism 1. Such dowels cooperate with corresponding recesses 16 in the anchoring element 4 or a connection piece (not illustrated) arranged suitably between the guide sleeve 11 and the joint mechanism 1.

One or more holes may be directly connected with the radially outer surface of the anchoring element 4, with the edges of the holes toward the surface forming cutting edges. Self-tapping is thus achieved when the body 5 is screwed into the bone 2. The removed bone tissue 17 is taken up inside the anchoring element 4 as illustrated in FIG. 5.

Since the thickness of the wall of the anchoring element 4 gradually decreases toward the insertion end 7 and/or since the element 4 has the longitudinal slits 8 and 9, the requirement for good deformation is fulfilled, thus greatly reducing the risk of concentrated stress which causes particular problems in prior art designs. The arrows B—B in FIG. 1 denote the flexibility of the open end 7, i.e. its ability to adjust to the surrounding tissue. The same applies to the arrows A—A.

Figure 5:
FIG. 5 is a cross-sectional view along the line 5—5 of FIG. 4.

The slits 8 and 9 may suitably be provided with cutting edges and, since the hollow cavity takes up the shavings 17, as illustrated in FIG. 5, the anchoring element 4 is, in itself, its own preparation tool. At the same time, optimum conditions for normal anatomical and physiological situations are ensured such that disturbance of the remaining biological tissue, i.e. marrow and bone tissue, is minimized.

Figure 2:
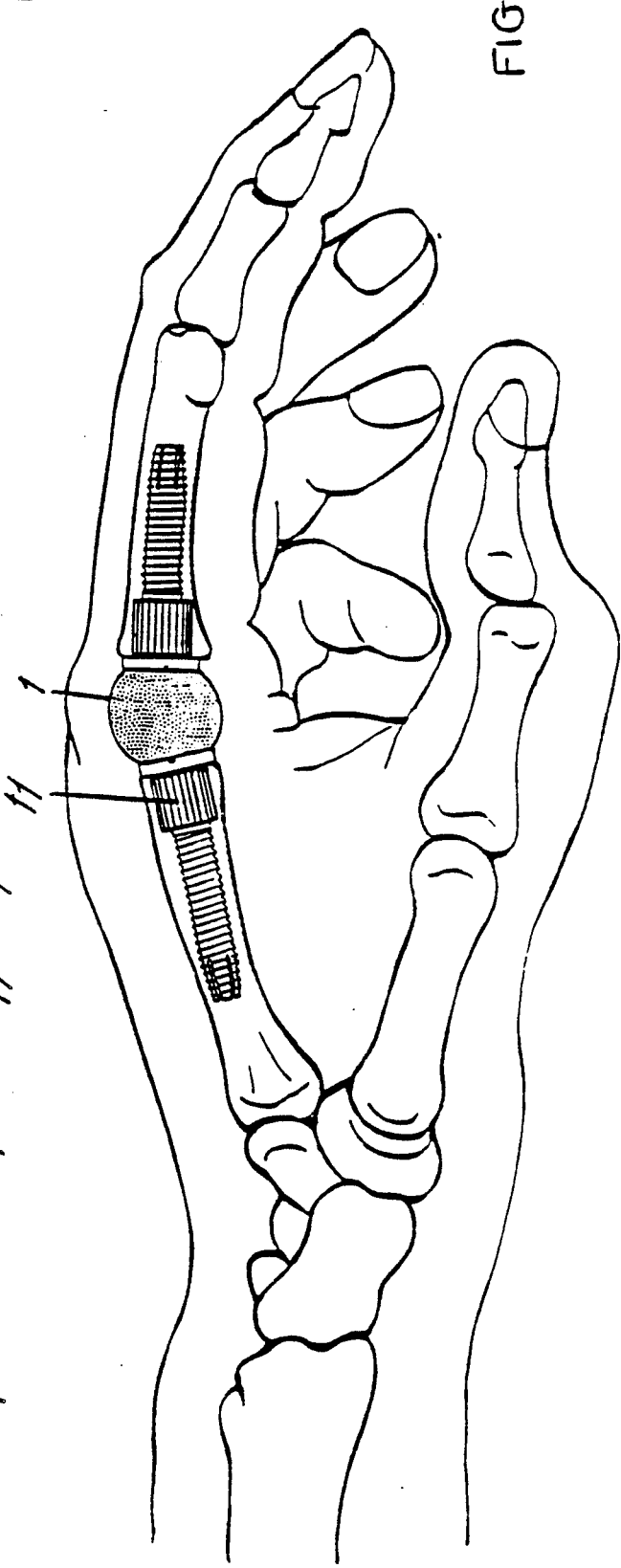
FIG. 2 shows a fully reconstructed finger joint.

FIG. 2 shows the joint reconstruction achieved with the anchoring element 4 in place.

Figure 3:
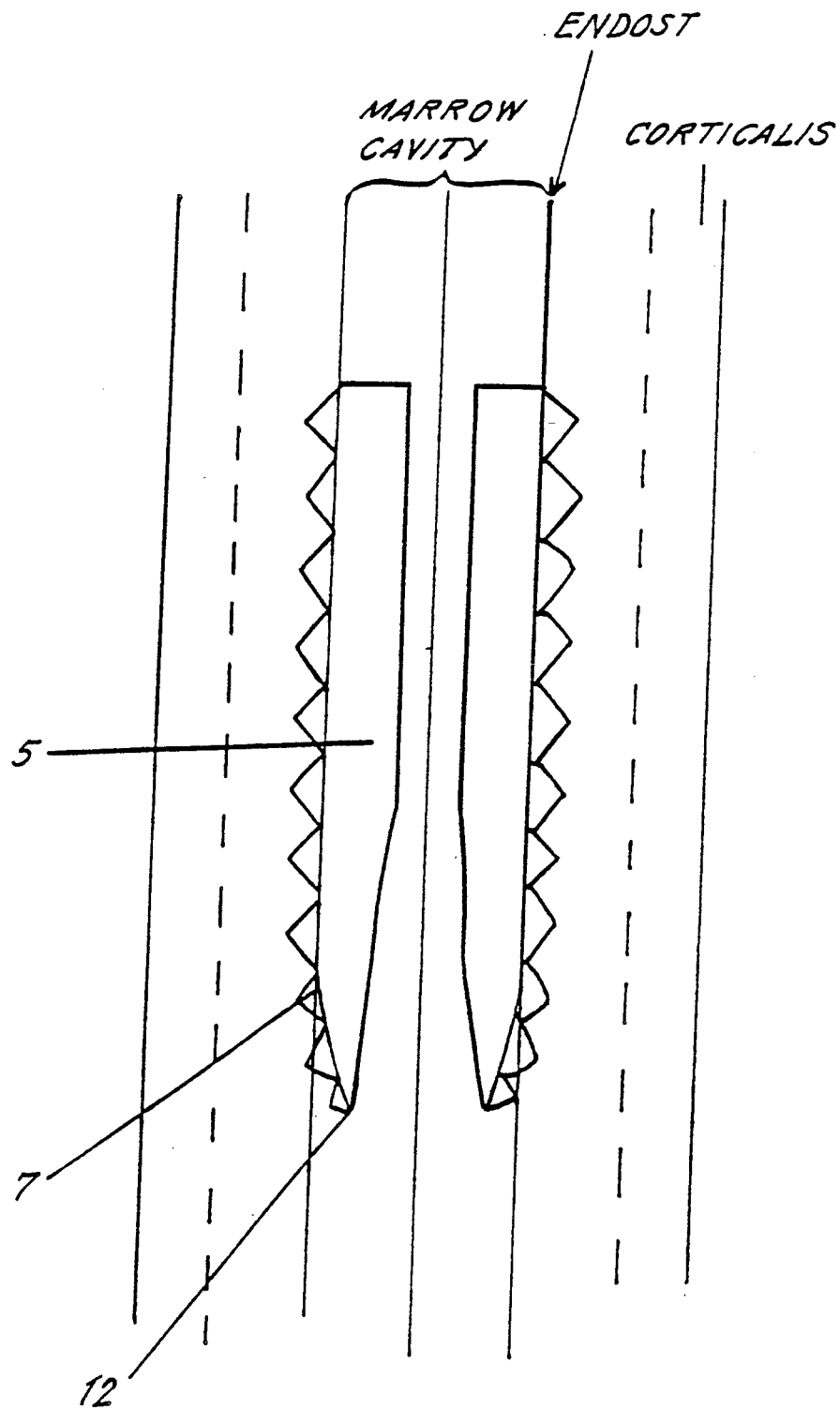
FIG. 3 illustrates how the anchoring element is located in the long bone.
Figure 4:
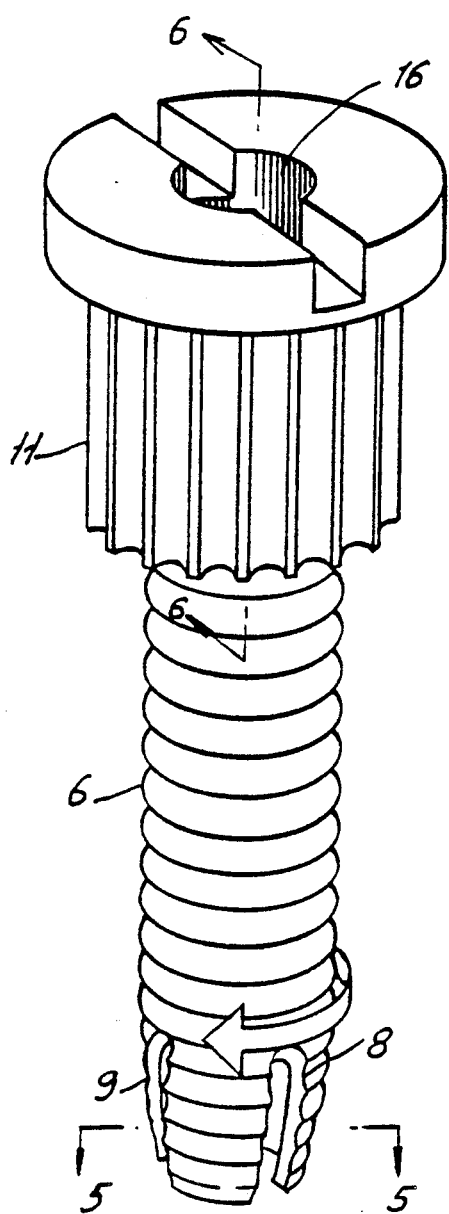
FIG. 4 is a perspective view of the anchoring element.

FIG. 3 illustrates how the anchoring element 4 is positioned in the bone 2. When in use, the anchoring element 4 is positioned in the boundary zone between marrow and bone tissue. The wall thickness of the sleeve-like body 5 decreases toward the slit insertion end 7, finishing in a cutting tapered edge 12. The edges of the longitudinal slits 8 may also be in the form of cutting edges. The shavings 17 produced when the anchoring element 4 is screwed into the marrow cavity are thus transferred to the hollow space inside the body 5 as illustrated in FIG. 5.

In operation, the part of the long bone 2 close to the joint is cut, thus exposing the marrow cavity. A probe (not illustrated) is then inserted into the marrow cavity to localize a suitable longitudinal axis for insertion of the anchoring element 4. The probe is used as a direction finder to center the anchoring element 4 as desired. A recess for the guide sleeve 11 is then carefully drilled in the exposed marrow cavity. After application of the guide sleeve 11, the sleeve-like body 5 is screwed down into the marrow cavity through the guide sleeve 11. The probe has of course been previously removed. The joint end 13 of the anchoring element 4 widens somewhat outwardly and upwardly as illustrated at 18 such that its diameter is slightly larger than the lower opening of the guide sleeve 11. Thus, a wedge effect will finally occur between the joint end 13 and the guide sleeve 11 (when the sleeve 11 is moved to the position illustrated in dotted lines in FIG. 6), so that both guide sleeve 11 and sleeve-like body 5 are positioned as desired.

The anchoring element 4 and the guide sleeve 11 consist of or are manufactured of titanium or are coated with titanium. The structure of the titanium surface is such that, at least over part of the relevant surface, integration is promoted. Advantageously, the surface may have irregularities consisting of micro-pitting, as described in Swedish patent 7902035-0, with pitting diameters of between 10 and 1000 nm, preferably 10-300 nm. Alternatively, the chemical composition of the titanium surface layer may be given certain positive tissue reactions, as described in Swedish patent 8505158-9, for instance.

Although the invention has been described in relation to a preferred embodiment thereof, many other variations and modifications and other uses will become apparent to those skilled in the art. It is preferred, therefore, that the invention be limited not by the specific disclosure herein, but only by the appended claims.

What is claimed is:

1. An anchoring element for supporting a joint mechanism, wherein said anchoring element is substantially rotationally symmetrical, at least partially hollow, and includes a material which is compatible with the tissue of a bone, said anchoring element having a surface which can be at least partially osseo-integrated with the tissue to achieve permanent endosteal anchorage in the longitudinal axis of the bone; and wherein said anchoring element comprises a sleeve-like body with a radially outer surface with external threads for screwing said anchoring element in to the bone; and wherein said sleeve-like body is deformable so as to reduce the risk of concentrated stress and so as to provide said anchoring element with an ability to adjust to the tissue.

2. The anchoring element of claim 1, wherein said material of said anchoring element is titanium.

3. The anchoring element of claim 1, wherein said surface of said anchoring element is coated with titanium.

4. The anchoring element of claim 1, wherein the joint mechanism is an element of a reconstructed finger joint.

5. The anchoring element of claim 1, wherein said surface of said anchoring element is a radially outer surface and is at least partially micropitted with diameters of between 10–300 nm.

6. The anchoring element of claim 5, further comprising holes directly connected to said radially outer surface, said holes having cutting edges at said radially outer surface.

7. The anchoring element of claim 1, wherein said sleeve-like body has a wall and an open insertion end, the thickness of said wall gradually decreasing toward said insertion end.

8. The anchoring element of claim 7, further comprising longitudinal slits through said wall, said slits extending from said insertion end toward the joint mechanism.

9. The anchoring element of claim 8, wherein said slits have cutting edges.

10. An anchoring element for supporting a joint mechanism, wherein said anchoring element is substantially rotationally symmetrical, at least partially hollow, and includes a material which is compatible with the tissue of a bone, said anchoring element having a surface which can be at least partially osseo-integrated with the tissue to achieve permanent endosteal anchorage in the longitudinal axis of the bone; and wherein said anchoring element comprise a deformable sleeve-like body with a radially outer surface with external threads for screwing said anchoring element into the bone;

wherein said anchoring element further comprises holes which are directly connected to said radially outer surface, said holes having cutting edges at said radially outer surface;

wherein said sleeve-like body has a wall and an open insertion end, the thickness of said wall gradually decreasing toward said insertion end; and wherein said anchoring element further comprises longitudinal slits through said wall, said slits extending from said insertion end toward the joint mechanism m; said slits having cutting edges; and wherein said sleeve-like body includes a joint end located close to the joint mechanism, and a guide sleeve, said joint end expanding somewhat conically int he direction of the joint mechanism, said joint end being positioned and secured in a lower end of said guide sleeve such that said guide sleeve surrounds said joint end.

11. The anchoring element of claim 10, wherein said joint end defines an open end facing the joint mechanism for detachably applying the joint mechanism to said anchoring element.

12. A joint reconstruction, comprising:

a joint mechanism adapted to be connected to a bone; and an anchoring element supporting said joint mechanism, said anchoring element being substantially rotationally symmetrical, at least partially hollow, and including a material which is compatible with the tissue of said bone, said anchoring element having a surface which is at least partially osseo-integrated with the tissue thereby achieving permanent endosteal anchorage in the longitudinal axis of said bone; and wherein said anchoring element comprises a sleeve-like body with a radially outer surface with external threads for screwing said anchoring element into said bone; and wherein said sleeve-like body is deformable so as to reduce the risk of concentrated stress and so as to provide said anchoring element with an ability to adjust to the tissue.

* * * * *